(12) United States Patent
Yuan et al.

(10) Patent No.: US 8,466,298 B2
(45) Date of Patent: Jun. 18, 2013

(54) HIGH SELECTIVELY POLYMERIC ADSORBENT BASED ON THE HYDROGEN BONDING INTERACTION AND THE USE THEREOF IN ISOLATION AND PURIFICATION OF ACTIVE COMPONENTS FROM GINGKO BILOBA EXTRACT

(75) Inventors: Zhi Yuan, Tianjin (CN); Chunhong Wang, Tianjin (CN); Rongfu Shi, Tianjin (CN); Jing Zhang, Shanghai (CN); Ping Ren, Langfang (CN); Yingchao Chen, Shanghai (CN)

(73) Assignee: Nankai University, Tianjin (CN)

( * ) Notice: Subject to any disclaimer, the term of this patent is extended or adjusted under 35 U.S.C. 154(b) by 2 days.

(21) Appl. No.: 13/119,371

(22) PCT Filed: Feb. 12, 2009

(86) PCT No.: PCT/CN2009/000150
§ 371 (c)(1),
(2), (4) Date: Mar. 16, 2011

(87) PCT Pub. No.: WO2010/060254
PCT Pub. Date: Jun. 3, 2010

(65) Prior Publication Data
US 2011/0218346 A1 Sep. 8, 2011

(30) Foreign Application Priority Data
Nov. 28, 2008 (CN) .......................... 2008 1 0153620

(51) Int. Cl.
*C07D 309/30* (2006.01)
*C08F 8/32* (2006.01)

(52) U.S. Cl.
USPC ........................... 549/263; 521/139; 525/183

(58) Field of Classification Search
USPC .................... 549/263, 295; 521/139; 525/183
See application file for complete search history.

(56) References Cited

U.S. PATENT DOCUMENTS 5,279,821 A * 1/1994 Hirayama et al. ......... 424/78.17
5,460,725 A * 10/1995 Stringfield ................... 210/690
6,475,534 B2 * 11/2002 Xie et al. ...................... 424/752

FOREIGN PATENT DOCUMENTS

| CN | 1449416 A | 10/2003 |
|---|---|---|
| CN | 1631518 A | 6/2005 |
| CN | 101050227 A | 10/2007 |
| CN | 101100495 A | 1/2008 |
| GB | 786148 A | 11/1957 |
| WO | 9633728 A | 10/1996 |

OTHER PUBLICATIONS

Ren et al., "Synthesis of high selectivity polymeric adsorbent and its application on the separation of ginkgo flavonol glycosides and terpene lactones," Reactive & Functional Polymers, vol. 68,Jan. 20, 2008, pp. 899-909.

Zha, Z., "Synthesis and applications of macro porous adsorption resins for separating flavones of Chinese traditional medicines," Chinese Doctoral Dissertations & Master's Theses Full-text Database (Master), Engineering Science and Technology I, vol. 02, Dec. 15, 2002.

Chandrasekaran et al., "Neuroprotective effects of bilobalide, a component of the Ginkgo biloba extract (EGb 761), in gerbil global brain ischemia", Brain Research vol. 922, Issue 2, Dec. 20, 2001, pp. 282-292.

Middleton et al., "The Role of Flavonol Glycosides and Carotenoids in Protecting Soybean from Ultraviolet-B Damage," Plant Physiol. (1993) 103:741-752.

Han et al., "Isolation and Purification of Terpene Lactones from Ginkgo Biloba," Chinese Traditional and Herbal Drugs, vol. 33, (2002), issue 11.

* cited by examiner

*Primary Examiner* — Golam M M Shameem
(74) *Attorney, Agent, or Firm* — Baker & Hostetler LLP

(57) ABSTRACT

Provided are a kind of high selectivity polymeric adsorbents with amide functional groups based on the hydrogen bonding interaction, which is prepared by adequately swelling a DVB-co-MA copolymer of 6% crosslinking degree as the initial resin with dimethyl formamide, performing an amination reaction by adding a diamine, soaking the dried resultant yellow resin with an acylating agent that is a dianhydride, and performing an acylation reaction to obtain the polymeric adsorbent with amide functional groups of the invention. The polymeric adsorbent of the invention can be used to effectively isolate and purify the active ingredients, i.e., flavones and lactones, from the extract of ginkgo leaf.

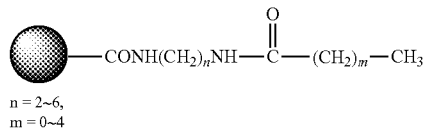

n = 2~6,
m = 0~4

3 Claims, No Drawings

HIGH SELECTIVELY POLYMERIC ADSORBENT BASED ON THE HYDROGEN BONDING INTERACTION AND THE USE THEREOF IN ISOLATION AND PURIFICATION OF ACTIVE COMPONENTS FROM GINGKO BILOBA EXTRACT

CROSS-REFERENCE TO RELATED APPLICATIONS

This application is a National Stage of International Patent Application No. PCT/CN 2009/000150, filed on Feb. 12, 2009, which claims priority to foreign Patent Application CN 2008 101 53 620.3, filed on Nov. 28, 2008, the disclosures of which are incorporated herein by reference in their entirety.

FIELD OF THE INVENTION

The present invention involves in the structural design for a kind of polymeric adsorbents and the isolation and purification of active components from natural plants, and particularly, relates to a method for synthesizing the high selectivity polymeric adsorbent with amide functional groups based on the hydrogen bonding interaction, and to a process for isolation of two kinds of active components, i.e. flavones and lactones, from ginkgo biloga extract using the synthesized polymeric adsorbent.

BACKGROUND OF THE INVENTION

With the changes in the life condition and living environment, human is experienced a greatly improved health level, infectious diseases are being or have been replaced by modern diseases, and the medical model of the human being is being changed from the mere treatment of the diseases to a combination of treatment, prevention, healthcare and rehabilitation. In addition, various alternative medicines and traditional medicines play an increasing role and the concept of "returning to nature" becomes very popular in world wide, and thus the natural drugs from green plants are paid more and more attention due to their high safety, unique pharmacological and physiological activities.

Modern medicinal research on ginkgo leaves is doubtless one of the highlights in the development of natural plant medicines. In early 70s, a rigorously standardized ginkgo biloga extract named EGb761, which is a mixture of flavonol glycosides (its content is 24% or more) and terpene lactones (sum of ginkgolides and bilobalides, the total content is 6% or more), was first produced in large scale by solvent extraction method in Germany, whereby a single phytomedicine with significant and stable therapeutic effects for cardiovascular and cerebrovascular diseases was developed and became the best-selling drug in Europe and attracted much attention in international medical and pharmaceutical domain (K. Chandrasekaran, Z. Mehrabian, B. Spinnewyn, K. Drieu, G. Fiskum, Brain Res. 922 (2001): 282). However, with extensive research, numerous pharmacological and clinical experiments demonstrate that the two main active components in ginkgo biloga extract, i.e. flavones and lactones, do not have the completely same pharmacologic actions (E. M. Middleton, A. H. Teramura, Plant Physiology, 103 (1993) 741), and the different combinations thereof in different ratios may achieve therapeutically different effects. Especially, since the research team led by P. Braquet in France firstly identified that ginkgolides had a strong and specific inhibition for platelet activating factor (PAF) receptors, as the currently most potent PAF receptor blocker, ginkgolides has been applied in many clinical researches for the treatments of, for example, asthma, endotoxin shock, reject reaction of organ transplantation, cardiovascular and cerebrovascular diseases, various inflammatory diseases, and the like, and achieved remarkable achievements. (P. Braquet, Drug. Future, 12 (1987) 643.) Since all the above pharmacologically and pharmacodynamically intensive studies on ginkgo leaves and pharmaceutical development of ginkgo preparation require urgently testing samples only containing the single principle component, it proposes a high demand for the isolation and purification of the two active components in ginkgo leaves. At present, the separating process described in a Japanese patent (J. Oreilly, WO 9633728, 1996) is predominantly adopted, which comprises a plurality of steps including solvent extraction, decoloration with active carbon, recrystallisation, and the like. However, such process is complicated with a great loss of the active components. Especially, it uses a large amount of organic solvent with a low boiling point and strong toxicity in the isolation, resulting in serious environmental pollution. In recent years, resin adsorption method shows unique advantages in extract and separation of natural productions. For example, it has the simple process and device, less investment and high extraction yield and may greatly reduce the production cost, when compared with conventional solvent extraction. Meanwhile, as this method uses less organic solvent, e.g. only water and alcohol, and most of the alcohol can be recovered, it is an environment-friendly technology and is highly competitive at the technical level. However, the adsorption selectivity of the existing polymeric adsorbents is too bad to be used to separate the components with similar property. Therefore, a satisfied result is hard to be obtained in the isolation of active components from ginkgo leaves, and auxiliary steps such as solvent extraction, decoloration with active carbon, and the like are still needed after adsorption process. Hence, the advantages of the adsorption method do not be exhibited. (Jinyu Han, Yingchun Yan, et. al., Isolation and Purification of Terpene Lactones from Ginkgo Biloba, Chinese Traditional and Herbal Drugs, Vol. 33, (2002), issue 11).

SUMMARY OF THE INVENTION

In order to overcome the above defects of the prior art, an object of the present invention is to provide a kind of high selectivity polymeric adsorbents with amide functional groups based on the hydrogen bonding interaction and the use thereof in isolation and purification of the active components from ginkgo biloda extract.

Based on the characteristic of the molecular structure of flavone and lactone, a novel high selectivity polymeric adsorbent with specific functional groups is designed and synthesized in the present invention, which has a highly improved adsorption ability for flavones so that flavones and lactones can be separated by only one step of "adsorption-desorption". Therefore, the process is easily operated, highly efficient and eco-friendly, and suitable for large-scale industrial production. Flavones and lactones can be separated completely by a one-step continuous process of "adsorption-desorption" to simultaneously obtain the two products, that is, the flavones extract without lactones and the lactones extract without flavones, which will provide a large amount of testing samples for the intensive pharmacological and pharmacodynamic studies, and thus be of great significance to the pharmaceutical research and exploitation of ginkgo leaves.

In order to accomplish the above object, the present invention discloses the high selectivity polymeric adsorbent with amide functional groups based on the hydrogen bonding interaction represented by the following structure formula:

n = 2~6,
m = 0~4 wherein, n=2~6, m=0~4, and the initial resin matrix is a DVB-co-MA copolymer of 6% crosslinking degree, which is in a spheric shape and has a particle size of 0.3~1.0 mm, an average pore size of 10~30 nm and a porosity of 50~65%.

The method for synthesizing the polymeric adsorbent according to the present invention is accomplished by the following steps.

First, as the initial resin, the DVB-co-MA copolymer with 6% crosslinking degree (the resin is in a spheric shape and has a particle size of 0.3~1.0 mm, an average pore size of 10~30 nm and a porosity of 50~65%) is dried sufficiently and put into a 3-neck flask, and then adequately swelled with N,N-dimethylformamide. A diamine that is 50~200% by weight of the initial resin is added as an amination agent, and the reaction is carried out for 8~12 h at a temperature of 60~140° C. After the reaction is finished, the reaction mixture is left to stand for cooling down to the room temperature, filtered and washed to give a yellow resin, wherein the reaction process is represented by the following scheme:

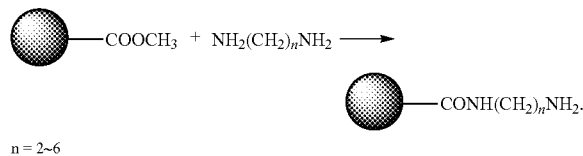

n = 2~6

Second, after dried, the yellow resin prepared by the above process is sufficiently soaked with an acylating agent of dianhydride in a 3-neck flask, wherein the amount of the dianhydride is 2~5 times of the weight of the yellow resin. Then the reaction temperature is raised up to 70~100° C., and the reaction is maintained for 7~10 hours. After the reaction is finished, the reaction mixture is left to stand for cooling to the room temperature, filtered and washed to obtain the polymeric adsorbent with amide functional groups of the present invention, which is numbered as Pnm (wherein, n=2~6, m=0~4). The reaction process is represented by the following scheme:

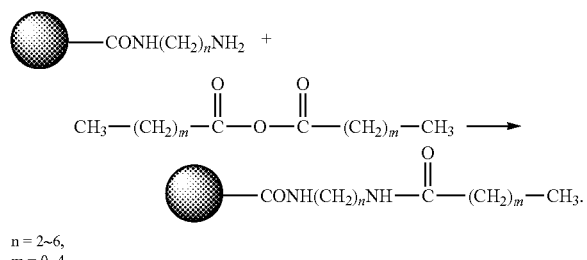

n = 2~6,
m = 0~4

The present invention further discloses the use of the synthesized polymeric adsorbent based on the hydrogen bonding interaction in isolation of flavones and lactones from the ginkgo biloda crude extract, which comprises the following steps.

First, a commercially available ginkgo biloda extract containing flavones of 24~26 wt % and lactones of 6~6.5 wt % is dissolved in an aqueous solution of ethanol/water (6:94~10:90, v/v) to prepare an adsorption solution with a concentration of 5~8 mg extract/ml.

Second, the polymeric adsorbent synthesized according to the present invention is packed into an absorption column having a ratio of diameter to length of 1:5~1:20.

Third, the adsorption solution is passed through the adsorption column at a flow rate of 0.5~1.0 BV/h at room temperature, wherein the adsorption capacity of the polymeric adsorbent is 1 ml adsorption solution/ml wet adsorbent. After adsorption, flavones are maintained in the adsorption column by absorption, while lactones flow out of the adsorption column since they have insufficient adsorption bonding force with the adsorbent and thus can not be adsorbed by the adsorbent.

Fourth, the effluent is collected and vacuum-dried to obtain a white solid, wherein the content of lactones is 30~50 wt % and flavones is not detectable by HPLC detection.

Fifth, the polymeric adsorbent is eluted with an aqueous solution of ethanol/water (60:40~80:20, v/v) at a desorption rate of 0.5~1.0 BV/h. The ethanol is recovered by vacuum distillation and the residue is vacuum dried to obtain a light yellow solid, wherein the content of flavones is 30~50 wt % and lactones is not detectable by HPLC detection.

ADVANTAGEOUS EFFECTS OF THE INVENTION

Based on the characteristic of the molecular structure of flavone and lactone, a novel high selectivity polymeric adsorbent with amide functional groups is designed and synthesized in the present invention, which has a highly improved adsorption ability for flavones through the specific action of hydrogen bonding, so that flavones and lactones can be separated by a one-step continuous process of "adsorption-desorption" to obtain simultaneously the two products, that is, the flavones extract without lactones and the lactones extract without flavones. The polymeric adsorbent synthesized according to the present invention has a high selectivity for the adsorption of flavones, and the process for the isolation of flavones and lactones established by the present invention is easy to be operated, highly efficient for the isolation and eco-friendly, and has a low production cost, while avoiding the use of large amount of highly toxic, easily volatile and flammable organic solvent, and thus has an important and actual application value in further pharmaceutical studies on ginkgo biloda extract.

BEST MODE FOR CARRYING OUT THE INVENTION

EXAMPLE 1

100 g of initial resin of DVB-co-MA copolymer with 6% crosslinking degree was added in a 500 ml 3-neck flask and fully swollen with 400 ml of N,N-dimethylformamide. 50 g of 1,2-ethylenediamine (i.e. an amination agent wherein n=2) was added and stirred to obtain a uniform mixture. The temperature was increased to 80° C. and the reaction was maintained for 10 hours. After the reaction finished, the reaction mixture was washed and a yellow resin was obtained.

100 g of the above yellow resin was added into a 500 ml 3-neck flask, followed by addition of 200 ml of succinic anhydride (i.e. the acylating agent, wherein m=2). After mixed well, the mixture was maintained for 9 hours at 100° C. After the reaction finished, the reaction mixture was washed and a light yellow resin was obtained, which is the polymeric adsorbent of the present invention numbered as P22.

EXAMPLE 2

100 g of initial resin of DVB-co-MA copolymer with 6% crosslinking degree was added in a 500 ml 3-neck flask and adequately swollen with 400 ml of N,N-dimethylformamide. 150 g of 1,6-hexamethylene diamine (i.e. an amination agent wherein n=6) was added and stirred to obtain a uniform mixture. The temperature was increased to 130° C. and the reaction was maintained for 12 hours. After the reaction finished, and the reaction mixture was washed to give a yellow resin.

100 g of the above yellow resin was added into a 500 ml 3-neck flask, followed by addition of 300 ml of malonic anhydride (i.e. an acylating agent wherein m=1). After mixed well, the mixture was maintained for 8 hours at 80° C. After the reaction finished, the reaction mixture was washed and a light yellow resin was obtained, which is the polymeric adsorbent of the present invention numbered as P61.

EXAMPLE 3

1 kg of initial resin of DVB-co-MA copolymer with 6% crosslinking degree was added in a 5 L 3-neck flask, and adequately swollen with 4 L of N,N-dimethylformamide. 1 kg of 1,2-ethylenediamine (i.e. an amination agent wherein n=2) was added and stirred to obtain a uniform mixture. The temperature was increased to 100° C. and the reaction was maintained for 12 hours. After the reaction finished, and the reaction mixture was washed and a yellow resin was obtained.

2 kg of the above yellow resin was added into a 5 L 3-neck flask, followed by addition of 4 kg of ethanedioic acid anhydride (i.e. an acylating agent wherein m=0). After mixed well, the mixture was maintained for 10 hours at 80° C. After the reaction finished, the reaction mixture was washed and a light yellow resin was obtained, which is the polymeric adsorbent of the present invention numbered as P20.

EXAMPLE 4

1 kg of initial resin of DVB-co-MA copolymer with 6% crosslinking degree was added in a 5 L 3-neck flask, and adequately swollen with 4 L of N,N-dimethylformamide. 1.5 kg of 1,4-butanediamine (i.e. an amination agent wherein n=4) was added and stirred to obtain a uniform mixture. The temperature was increased to 110° C. and the reaction was maintained for 10 hours. After the reaction finished, and the reaction mixture was washed and a yellow resin was obtained.

1.5 kg of the above yellow resin was added in a 5 L 3-neck flask, followed by addition of 6 kg of adipic anhydride (i.e. an acylating agent wherein m=4). After mixed well, the mixture was maintained for 10 hours at 100° C. After the reaction finished, the reaction mixture was washed and a light yellow resin was obtained, which is the polymeric adsorbent of the present invention numbered as P44.

EXAMPLE 5

100 g of initial resin of DVB-co-MA copolymer with 6% crosslinking degree was added in a 500 ml 3-neck flask, and adequately swollen with 400 ml of N,N-dimethylformamide. 200 g of 1,5-pentamethylene diamine (i.e. an amination agent wherein n=2) was added thereto and stirred to obtain a uniform mixture. The temperature was increased to 80° C. and the reaction was maintained for 10 hours. After the reaction finished, and the reaction mixture was washed and a yellow resin was obtained.

100 g of the above yellow resin was added in a 500 ml 3-neck flask, followed by addition of 500 ml of succinic anhydride (i.e. an acylating agent wherein m=2). After mixed well, the mixture was maintained for 9 hours at 100° C. After the reaction finished, the reaction mixture was washed and a light yellow resin was obtained, which is the polymeric adsorbent of the present invention numbered as P52.

EXAMPLE 6

240 mg of ginkgo bilida extract containing flavones of 24% (w %) and lactones of 6% (w %) was dissolved in 40 ml aqueous solution of 7% ethanol (v/v) and an adsorption solution was obtained, wherein the concentration of the adsorption solution was 6.0 mg extract/ml. The adsorption solution was passed at the adsorption rate of 1.0 BV/h through a adsorption column (30 cm×18 mm, I.D.) packed with 40 ml of wet adsorbent P44 of the present invention. After the adsorption finished, the effluent was collected and the adsorption column was washed with deionized water. Then the adsorption column was eluted with an aqueous solution of 80% ethanol (v/v) at the eluting rate of 0.5 BV/h and the eluate was collected. The effluent and the eluate were evaporated and vacuum dried respectively to obtain two products. One was a white powder obtained from the evaporation of the effluent, wherein the content of lactones was 30.2% (w %) and flavones was not detectable by HPLC detection; and the other was a light yellow powder obtained from the evaporation of the eluate, wherein the content of flavones was 36.3% (w %) and lactones was not detectable by HPLC detection.

EXAMPLE 7

2800 mg of ginkgo bilida extract containing flavones of 25.2% (w %) and lactones of 6.3% (w %) was dissolved in 400 ml aqueous solution of 10% ethanol (v/v) and an adsorption solution was obtained, wherein the concentration of the adsorption solution was 7.0 mg extract/ml. The adsorption solution was passed at the adsorption rate of 0.5 BV/h through a adsorption column (50 cm×50 mm, I.D.) packed with 400 ml of wet adsorbent P20 of the present invention. After the adsorption finished, the effluent was collected and the adsorption column was washed with deionized water. Then the adsorption column was eluted with an aqueous solution of 70% ethanol (v/v) at the eluting rate of 1.0 BV/h and the eluate was collected. The effluent and the eluate were evaporated and vacuum dried respectively to obtain two products. One was a white powder obtained from the evaporation of the effluent, wherein the content of lactones was 48.3% (w %) and flavones was not detectable by HPLC detection; and the other was a light yellow powder obtained from the evaporation of the eluate, wherein the content of flavones was 47.3% (w %) and lactones was not detectable by HPLC detection.

EXAMPLE 8

600 mg of ginkgo bilida extract containing flavones of 24% (w %) and lactones of 6% (w %) was dissolved in 120 ml aqueous solution of 8% ethanol (v/v) and an adsorption solution was obtained, wherein the concentration of the adsorption solution was 5.0 mg extract/ml. The adsorption solution was passed at the adsorption rate of 0.8 BV/h through a adsorption column (40 cm×40 mm, I.D.) packed with 120 ml of wet adsorbent P61 of the present invention. After the adsorption finished, the effluent was collected and the adsorption column was washed with deionized water. Then the adsorption column was eluted with an aqueous solution of 80% ethanol (v/v) at the eluting rate of 0.8 BV/h and the eluate was collected. The effluent and the eluate were evaporated and vacuum dried respectively to obtain two products. One was a white powder obtained from the evaporation of the effluent, wherein the content of lactones was 30.1% (w %) and flavones was not detectable by HPLC detection; and the other was a light yellow powder obtained from the evaporation of the eluate, wherein the content of flavones was 41.3% (w %) and lactones was not detectable by HPLC detection.

EXAMPLE 9

3200 mg of ginkgo bilida extract containing flavones of 24.7% (w %) and lactones of 6.1% (w %) was dissolved in 400 ml aqueous solution of 10% ethanol (v/v) and an adsorption solution was obtained, wherein the concentration of the adsorption solution was 8.0 mg extract/ml. The adsorption solution was passed at the adsorption rate of 0.5 BV/h through a adsorption column (50 cm×50 mm, I.D.) packed with 400 ml of wet adsorbent P22 of the present invention. After the adsorption finished, the effluent was collected and the adsorption column was washed with deionized water. Then the adsorption column was eluted with an aqueous solution of 70% ethanol (v/v) at the eluting rate of 1.0 BV/h and the eluate was collected. The effluent and the eluate were evaporated and vacuum dried respectively to obtain two products. One was a white powder obtained from the evaporation of the effluent, wherein the content of lactones was 31.3% (w %) and flavones was not detectable by HPLC detection; and the other was a light yellow powder obtained from the evaporation of the eluate, wherein the content of flavones was 32.3% (w %) and lactones was not detectable by HPLC detection.

EXAMPLE 10

220 mg of ginkgo bilida extract containing flavones of 24.1% (w %) and lactones of 6.1% (w %) was dissolved in 40 ml aqueous solution of 10% ethanol (v/v) and an adsorption solution was obtained, wherein the concentration of the adsorption solution was 5.5 mg extract/ml. The adsorption solution was passed at the adsorption rate of 0.8 BV/h through a adsorption column (30 cm×18 mm, I.D.) packed with 40 ml of wet adsorbent P52 of the present invention. After the adsorption finished, the effluent was collected and the adsorption column was washed with deionized water. Then the adsorption column was eluted with an aqueous solution of 70% ethanol (v/v) at the eluting rate of 1.0 BV/h and the eluate was collected. The effluent and the eluate were evaporated and vacuum dried respectively to obtain two products. One was a white powder obtained from the evaporation of the effluent, wherein the content of lactones was 32.5% (w %) and flavones was not detectable by HPLC detection; and the other was a light yellow powder obtained from the evaporation of the eluate, wherein the content of flavones was 31.8% (w %) and lactones was not detectable by HPLC detection.

The invention claimed is:

1. A high selectivity polymeric adsorbent with amide functional groups based on the hydrogen bonding interaction represented by the following formula:

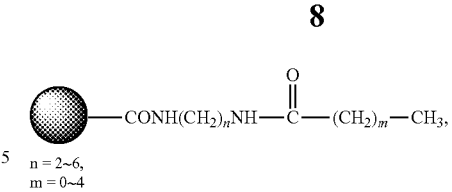

n = 2~6,
m = 0~4 wherein, n=2~6, m=0~4 and the initial resin matrix is a DVB-co-MA copolymer of 6% crosslinking degree and the DVB-co-MA copolymer is in a spheric shape and has a particle size of 0.3~1.0 mm, an average pore size of 10~30 nm and a porosity of 50~65%.

2. A method for synthesizing the polymeric adsorbent according to claim 1, characterized in that the method comprises the following steps:

first, as the initial resin, the DVB-co-MA copolymer with 6% crosslinking degree is dried sufficiently and put into a 3-neck flask, and then adequately swelled with N,N-dimethyl formamide; a diamine that is 50~200% of the weight of the initial resin is added as an amination agent, and the reaction is carried out for 8~12h at a temperature of 60~140° C.; after the reaction is finished, the reaction mixture is left to stand for cooling down to the room temperature, filtered and washed to give a yellow resin, wherein the reaction process is represented by the following scheme:

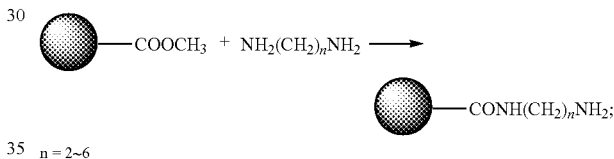

n = 2~6 second, after dried, the yellow resin prepared by the above process is sufficiently soaked with an acylating agent of dianhydride in a 3-neck flask, wherein the amount of the dianhydride is 2~5 times of the weight of the yellow resin; and then the reaction temperature is raised up to 70~100° C. and the reaction is maintained for 7~10h; after the reaction is finished, the reaction mixture is left to stand for cooling down to the room temperature, filtered and washed to obtain the present polymeric adsorbent with amide functional groups, the reaction process is represented by the following scheme:

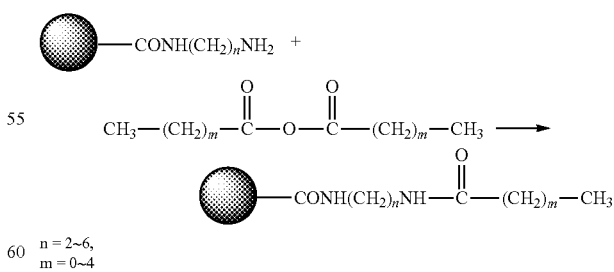

n = 2~6,
m = 0~4 the polymeric adsorbent is numbered as Pnm, wherein n=2~6, m=0~4, and the DVB-co-MA copolymer is in a spheric shape and has a particle size of 0.3~1.0 mm, an average pore size of 10~30 nm and a porosity of 50~65%.

3. A method of isolating flavones and lactones from ginkgo biloda crude extract, the method comprising the following steps:
- dissolving a commercial ginkgo biloda extract containing flavones of 24~26% and lactones 6~6.5% in an aqueous solution of ethanol/water (6:94~10:90 (V/V) to prepare an adsorption solution with a concentration of 5~8 mg extract/ml;
- packing the polymeric adsorbent of claim 1 into an adsorption column having a ratio of diameter to length of 1:5~1:20;
- passing the adsorption solution through the adsorption column at a flow rate of 0.5~1.0 BV/h at room temperature, wherein the adsorption capacity of the polymeric adsorbent is 1 ml adsorption solution/ml wet adsorbent; and after adsorption, flavones are maintained in the adsorption column by adsorbed by the polymeric adsorbent, while lactones flow out of the adsorption column since they have insufficient adsorption bonding force with the polymeric adsorbent and thus can not be adsorbed by the polymeric adsorbent; and
- collecting, evaporating and vacuum-drying the effluent to obtain a white solid, wherein the content of lactones is 30~50 wt % and flavones is not detectable by HPLC detection;
- eluting the polymeric adsorbent with an aqueous solution of ethanol/water (60:40~80:20, v/v) at a desorption rate of 0.5~1.0 BV/h; and
- recovering ethanol in the eluate through vacuum distillation, and vacuum-drying the residue to obtain a light yellow solid, wherein the content of flavones is 30~50 wt % and lactones is not detectable by HPLC detection.

* * * * *